United States Patent
Atkinson et al.

(10) Patent No.: US 8,800,393 B2
(45) Date of Patent: Aug. 12, 2014

(54) PHASE SAMPLER PROBE AND METHOD OF USING THEREOF

(75) Inventors: Malcolm Atkinson, Inverurie (GB);
Muhammad Adeel Zahid Khan, Aberdeen (GB); Bernard Theron, Aberdeen (GB)

(73) Assignee: Schlumberger Technology Corporation, Sugar Land, TX (US)

( * ) Notice: Subject to any disclaimer, the term of this patent is extended or adjusted under 35 U.S.C. 154(b) by 653 days.

(21) Appl. No.: 13/060,200

(22) PCT Filed: Aug. 27, 2009

(86) PCT No.: PCT/EP2009/006212
§ 371 (c)(1),
(2), (4) Date: Apr. 27, 2011

(87) PCT Pub. No.: WO2010/022942
PCT Pub. Date: Mar. 4, 2010

(65) Prior Publication Data
US 2011/0198079 A1     Aug. 18, 2011

Related U.S. Application Data

(60) Provisional application No. 61/092,308, filed on Aug. 27, 2008.

(51) Int. Cl.
*G01N 1/20* (2006.01)
(52) U.S. Cl.
USPC ........................................... 73/863.51

(58) Field of Classification Search
USPC ............ 166/264; 73/863.41, 863.86, 864.74, 73/863.58
See application file for complete search history.

(56) References Cited

U.S. PATENT DOCUMENTS

| | | | |
|---|---|---|---|
| 3,841,156 A | 10/1974 | Wolfe | |
| 4,346,609 A | 8/1982 | Diesel | |
| 4,442,720 A * | 4/1984 | Apley et al. | ................ 73/863.31 |
| 5,161,417 A | 11/1992 | Strong et al. | |
| 6,470,755 B1 * | 10/2002 | Beachey et al. | ................ 73/756 |
| 6,536,272 B1 | 3/2003 | Houston et al. | |
| 7,143,638 B1 | 12/2006 | Scott | |
| 2005/0223829 A1 | 10/2005 | Mayeaux | |
| 2007/0193373 A1 | 8/2007 | Xie et al. | |

FOREIGN PATENT DOCUMENTS

| | | |
|---|---|---|
| EP | 0023110 | 1/1981 |
| EP | 1645863 | 4/2006 |
| GB | 2319620 | 5/1998 |
| SU | 1177715 | 9/1985 |
| WO | WO 2006037565 A1 * | 4/2006 |

* cited by examiner

*Primary Examiner* — Peter Macchiarolo
*Assistant Examiner* — Tamiko Bellamy
(74) *Attorney, Agent, or Firm* — Cameron R. Sneddon

(57) ABSTRACT

An apparatus and method for selectively capturing substantially separate phases from a multiphase fluid mixture flowing through a flowline. The apparatus is preferably substantially aerofoil shaped, and includes sample ports which are positioned on the apparatus in such an orientation that takes advantage of the low density and high density flow around the aerofoil shape, as well as the pressure distribution around the aerofoil shape.

17 Claims, 2 Drawing Sheets

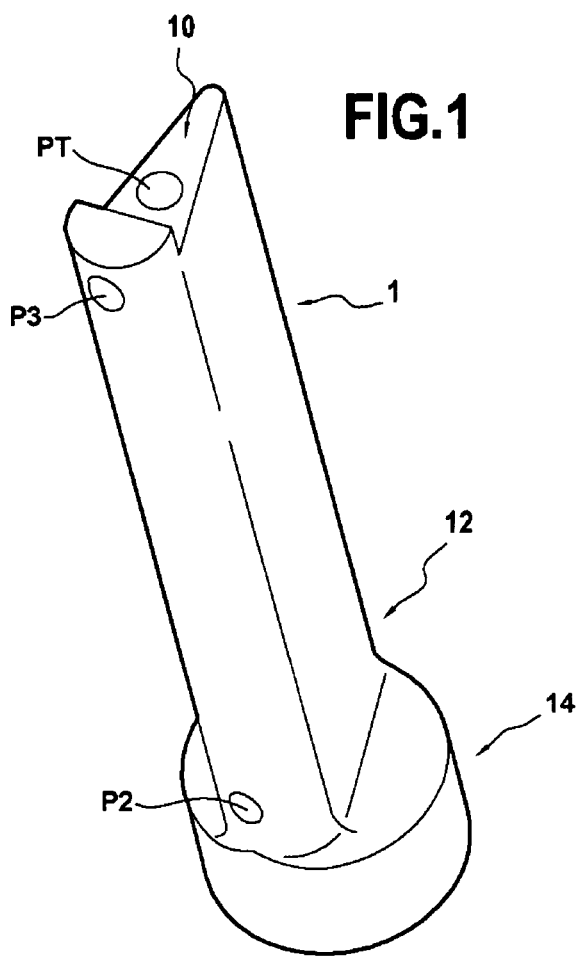
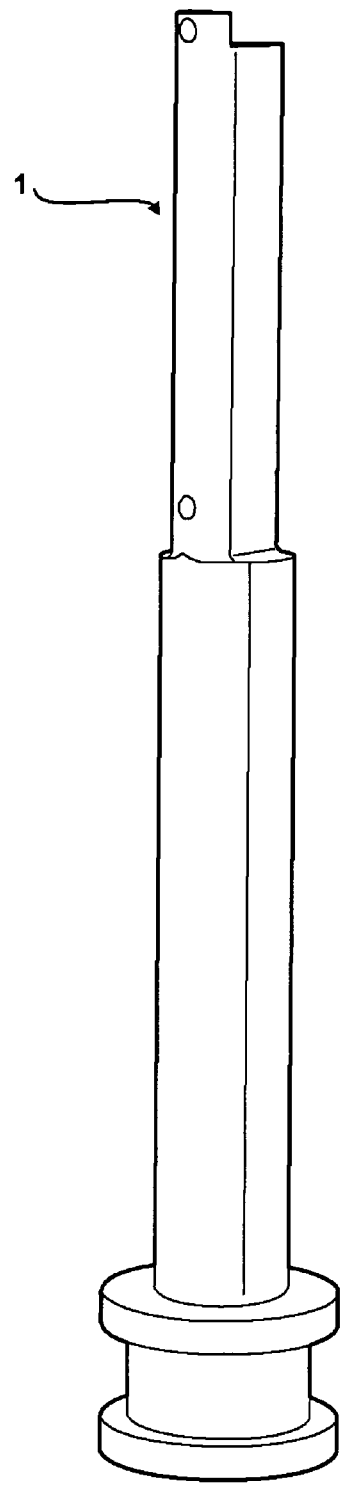
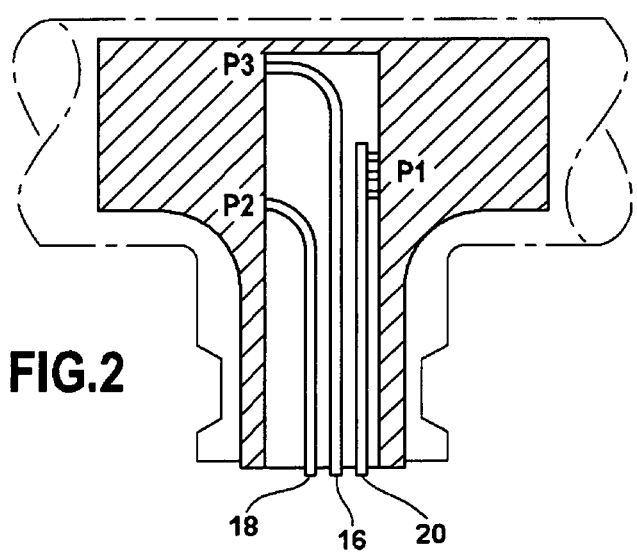

PHASE SAMPLER PROBE AND METHOD OF USING THEREOF

CROSS-REFERENCE TO RELATED APPLICATION

The present application is based on and claims priority to U.S. Provisional Patent Application No. 61/092,308, filed Aug. 27, 2008.

TECHNICAL FIELD

The present disclosure is directed to an apparatus and method for sampling fluid samples from a multiphase fluid mixture.

BACKGROUND ART

Sampling apparatus used to sample various phases of a multiphase fluid mixture from a hydrocarbon well is known, e.g., see EP1645863 and WO2006037565, and incorporated herein by reference. While such apparatus provides many advantages, improvements in methods and apparatus for selective enriched fluid sampling from a multiphase fluid mixture are desirable.

SUMMARY OF THE DISCLOSURE

Therefore, there is a need for a method and apparatus (which also may be referred to herein as a "system") that addresses discovered problems with existing systems and methods for sampling a single phase or a substantially single phase from a multiphase fluid stream. The above and other needs and problems are addressed by the present invention, exemplary embodiments of which are discussed below and illustrated in the figures.

The present disclosure is directed to a device and method for capturing selective enriched fluid samples from a multiphase fluid mixture flowing into and through a main pipe (also referred to herein as a "main flowline" or "main conduit") at low to high flow rates. The sample ports are located in the device in such an orientation that enriched samples can be individually collected for high liquid densities, low liquid densities and gas. The device and method provide sampling ports at varying pressures in a multiphase fluid mixture flow. The difference(s) in pressure(s) provide the force to drive the sampled mixture from the main pipe into externally located analysis equipment and then discharge the fluid back into the main flowline. The device has no moving parts and requires no external power source or fluid drive.

In a first aspect of the present invention, a probe is provided for selectively capturing substantially separate phases from a multiphase fluid mixture flowing through a flowline. The probe preferably comprises a probe body substantially having the shape of an aerofoil, including a terminal end, a basal end, a front portion, a back portion, and lateral portions disposed therebetween; a first port positioned on the probe body facing in a first direction relative to fluid flowing through a flowline; and a second port positioned on the probe body facing in a second direction, which is different from the first direction.

In an exemplary embodiment of the first aspect, the first port is positioned at the front portion of the probe, and the second port is positioned at the back portion of the probe. In an alternative embodiment, however, the second port may be positioned at the lateral portion of the probe.

The first port is preferably an open end of a first conduit included in the probe body, and the second port is an open end of a second conduit included in the probe body. The second port may further comprise a plurality of open ends of the second conduit. Further according to the first aspect of the present invention, the probe may include a third port positioned on the probe body facing in the first direction. As such, the third port may be an open end of a third conduit included in the probe body.

In a second aspect of the present invention, a probe is provided for selectively capturing substantially separate phases from a multiphase fluid mixture flowing through a flowline. The probe preferably comprises a probe body substantially having the shape of an aerofoil, including a terminal end, a basal end, a front portion, a back portion, and lateral portions disposed therebetween; a first port positioned on the front portion of the probe body adapted to capture a relatively high density fluid phase from the multiphase fluid flowing through the flowline; and a second port positioned on the back portion of the probe body adapted to capture a relatively low density fluid phase from the multiphase fluid flowing through the flowline.

In accordance with the second aspect, the probe may further comprise a third port positioned on one of the lateral portions of the probe body adapted to discard one of the captured phases back into the flowline.

In a third aspect of the present invention, a probe is provided for selectively capturing substantially separate phases from a multiphase fluid mixture flowing through a flowline. The probe preferably comprises a probe body substantially having the shape of an aerofoil, including a terminal end, a basal end, a front portion, a back portion, and lateral portions disposed therebetween; a first port positioned on the front portion of the probe body adapted to capture a predominately oil phase from the multiphase fluid flowing through the flowline; a second port positioned on the front portion of the probe body adapted to capture a predominately water phase from the multiphase fluid flowing through the flowline; and a third port positioned on the back portion of the probe body adapted to capture a predominately gas phase from the multiphase fluid flowing through the flowline.

In accordance with the third aspect, the first port may be positioned near the terminal end of the probe body, and the second port may be positioned near the basal end of the probe body. The third port may further be adapted to discard the any phase of the multiphase fluid back into the flowline.

In accordance with all aspects of the present invention, the probe may further include a port positioned at the terminal end of the probe body adapted to measure the flowline pressure.

In a fourth aspect of the present invention, a method is provided for selectively capturing substantially separate phases from a multiphase fluid mixture flowing through a flowline. The method comprising the steps of placing a probe, according to any aspects described herein, in the flowline, wherein the probe is oriented such that at least one port faces upstream with respect to the direction of flow of the multiphase fluid mixture; and the at least one port facing upstream selectively capturing a fluid which has a relatively high density from the multiphase fluid mixture flowing through the flowline.

According to the fourth aspect, the method further comprising the step of at least one other port not facing upstream selectively capturing a fluid which has a relatively low density from the multiphase fluid mixture flowing through the flowline. The at least one other port not facing upstream may selectively discard at least one captured fluid into the flowline.

In accordance with the present invention, the multiphase fluid mixture may comprise hydrocarbon oil, water and gases. Further in accordance with the present invention, the fluid which has a relatively low density may include substantially the hydrocarbon oil, and the fluid which has a relatively high density may include substantially the water. However, the fluid which has a relatively low density may include substantially the gases, and the fluid which has a relatively high density may include substantially the hydrocarbon oil or water.

Still other aspects, features, and advantages of the present invention are readily apparent from the entire description thereof, including the figures, which illustrate a number of exemplary embodiments and implementations. The present invention is also capable of other and different embodiments, and its several details can be modified in various respects, all without departing from the spirit and scope of the present invention. Accordingly, the drawings and descriptions are to be regarded as illustrative in nature, and not as restrictive.

BRIEF DESCRIPTION OF THE DRAWINGS

Various aspects and embodiments of the present invention are described below in the appended drawings to assist those of ordinary skill in the relevant art in making and using the subject matter hereof. In reference to the appended drawings, which are not intended to be drawn to scale, like reference numerals are intended to refer to identical or similar elements. For purposes of clarity, not every component may be labeled in every drawing.

FIG. 1 depicts a perspective view of an aerofoil shaped probe in accordance with an exemplary embodiment of the present invention.

FIG. 2 depicts a cross-sectional view of an exemplary arrangement of ports in the probe of FIG. 1.

FIG. 3 depicts an exemplary placement of the probe of FIG. 1 mounted on a sampling device.

DETAILED DESCRIPTION

Figure 1A:
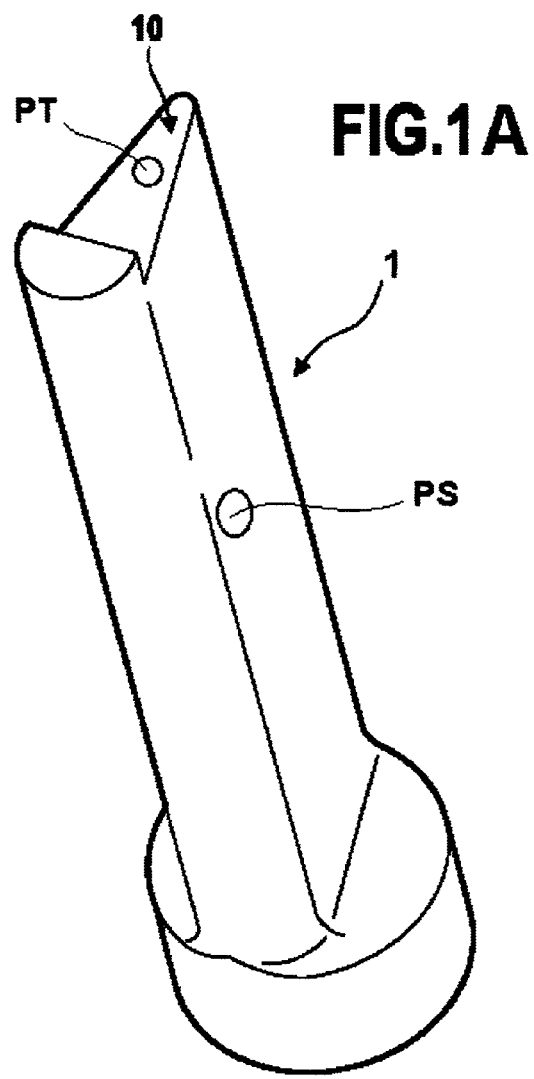
FIG. 1A depicts a perspective view of an aerofoil shaped probe in accordance with an alternative embodiment of the present invention.

Various embodiments and aspects of the present disclosure will now be described in detail with reference to the accompanying figures. The terminology and phraseology used herein is solely used for descriptive purposes and should not be construed as limiting in scope. Language such as "including," "comprising," "consisting of," "having," "containing," or "involving," and variations thereof, is intended to be broad and encompass the subject matter listed thereafter, equivalents, and additional subject matter not recited.

The design of an aerofoil shaped probe of this invention is aimed towards capturing a predominant phase from a multiphase fluid mixture flowing through a flowline. The probe may be used with any suitable existing apparatus for sampling fluid enriched in a selected phase from a multiphase fluid mixture, e.g., with ASD PHASE SAMPLER provided by SCHLUMBERGER. A need for such a probe arises for different reasons, e.g., in order to cope with the requirements of a large diameter flow pipe (i.e., VX88 by SCHLUMBERGER) with high flow velocity, as well as the need to measure or analyze fluid without permanently removing a sample from the fluid flowline. Thus, the existing PHASE SAMPLER probes required additional modifications at least for the above exemplary reason. After careful tests and analysis were conducted, the exemplary aerofoil shaped body design presented herein provides significant advantages in terms of vibrational aspects and stress capabilities that can sustain high flow rates. The aerofoil shape has several advantages, including, without limitations, reduction of the drag forces on the probe and hence the avoidance of the lock in frequency ranges. Additionally, the aerofoil shape can be designed according to a specific pressure boundary and required fluid dynamics capable of sampling a predetermined phase flowing around the probe, and discarding any predetermined phase back into the flowline. The sample ports in the aerofoil body are drilled in a similar fashion as to represent the orientation of the existing probes.

The design for the device of this invention enables continuous, self driven, sampling stream flow. The geometry and shape of the phase probe provides sampling ports at varying pressures. The pressure at a sampling port may be higher than, equal to, or lower than the main flowing pressure, which is the pressure in a main pipe which carries the multiphase fluid mixture. The main flowing pressure is produced by a multiphase fluid mixture flowing in the main pipe, usually at high flow rates. The term "multiphase fluid mixture" may also be referred to as the "main flow". This pressure difference will be used to drive the sample mixture through the probe and external equipment and then back into the probe to exit into the main flow. The external equipment may contain analysis devices which measure properties of the fluid samples.

The multiphase fluid mixture may be any fluid which includes several phases, e.g., a multiphase fluid mixture from a hydrocarbon(s) producing well. As is known, such mixture includes hydrocarbons (usually in the form of oil), water and gases.

Aerofoil Probe

The aerofoil shaped probe preferably comprises a one piece design having holes, or ports, appropriately positioned (i.e. by drilling) in order to carry out selective sampling in the high flow rate medium. The probe may be used with a variety of phase sampling devices, such as the SCHLUMBERGER PHASE SAMPLER with slight modifications to the existing PHASE SAMPLER parts, which may include, but is not limited to, a probe column, a column stud and gaskets in order to perform operations in a high flow rate environment. Due to the uniqueness of the shape and the ability to withstand high flow rates, while avoiding any lock in frequency ranges caused by resonance, the aerofoil shaped probe can be used with other future sampling equipments for selectively capturing substantially separate phases from multiphase fluid mixture samples.

Referring now to the drawings, there are illustrated an exemplary method and apparatus to capture selective various phases from a multiphase fluid mixture according to exemplary aspects of the present invention.

FIG. 1 is a perspective view of a model of the aerofoil shaped probe according to an embodiment of the present invention. The probe 1 is shown to include two ports P2/P3 at a front portion thereof which faces the upstream of the main flow in the flowline. The ports P2/P3 are adapted to capture fluid samples. The probe 1 may further include an additional port, or a plurality of small ports, P1 adapted to capture fluid samples at the back portion of the probe 1 which faces the downstream of the main flow in the flowline. In an exemplary implementation, the port(s) P2/P3 at the front portion capture the higher density fluid, such as oil or water; and the port(s) P1 at the back portion capture the lower density fluid, such as gas. Further illustrated in FIG. 1, the aerofoil shaped probe 1 includes a terminal end 10, a basal end 12 and a base 14. It should be understood, that any number of ports may be appropriately positioned along the front portion, back portion, terminal end, basal end, or lateral portions of the probe 1 to selectively capture the desired phase of fluid. As an example, FIG. 1A depicts a perspective view of an aerofoil shaped probe 1 showing a port PS on a lateral portion of the probe 1 adapted either to withdraw fluid from, or discard fluid into, the flowline. In another embodiment of the present invention, the probe 1 may further include a port PT positioned at the terminal end preferably adapted to measure the flowline pressure, but may also be adapted for sampling.

FIG. 2 illustrates schematically a cross-sectional view of a portion of the exemplary aerofoil shaped probe disposed in a flowline according to an aspect of the present invention. As shown in FIG. 2, the probe includes a first conduit 16 terminating with a port P3, a second conduit 18 terminating with a port P2, and a third conduit 20 terminating with multiple ports, such as four ports P1. The first, second and third conduits 16, 18 and 20, are shown to be substantially vertically extending in the probe body, having an open end to define the ports P3, P2, and P1. The ports P3 and P2 are oriented in substantially the same first direction, and the ports P1 are oriented in substantially the same second direction, which is opposite to the first direction.

In the exemplary device and method, the aerofoil shaped probe 1 of the present invention is placed in the flow of a multiphase fluid mixture flowing from a hydrocarbon, e.g., crude oil, well. The probe 1 is oriented such that the port(s) P1 faces downstream with respect to the direction of flow of the multiphase mixture, and the ports P2 and P3 upstream relative to the direction of flow of the multiphase mixture. The port(s) P1 capture(s) at least one gas sample, the port P2 captures relatively high density fluid, i.e., primarily water, and the port P3 captures relatively low density fluid, i.e., primarily oil.

Control of the fluid flow through any of the ports P1, P2, and P3 may be individually controlled by a single valve, or plurality of valves, and/or a piston or pump (not shown). In an exemplary embodiment of a closed loop system, a piston or pump will not be necessary due to the pressure difference created by the fluid dynamics design of the probe 1. That is, a pressure difference will exist between the front portion, lateral portion and back portion of the probe 1, where the highest pressure will be experienced at the front portion facing upstream of the flowline and the lowest pressure will be experienced at the lateral or back portion facing downstream of the flowline. The pressure difference may be used to withdraw fluid at the higher pressure portion, perform tests/analysis, and then discard the fluid into the flowline at the lower pressure portion.

In an exemplary embodiment of an open loop system, a pump or piston may be used, although not entirely necessarily, to withdraw the fluid from any portion of the probe 1 to perform tests/analysis without discarding back into the flowline.

Referring now to FIG. 3, a perspective view of the aerofoil shaped probe 1 is shown having an attachment means for attaching to a sampling device according to an embodiment of the present invention. The aerofoil shaped probe 1 may be permanently positioned in the flowline or may be selectively insertable and retractable from the flowline. The probe 1 is preferably positioned in a substantially vertical orientation in the flowline; however, it is contemplated that the probe may be positioned in any suitable orientation to selectively capture substantially separate phases.

Although only a few embodiments of the present invention have been described in detail above, those of ordinary skill in the art will readily appreciate that many modifications are possible without materially departing from the teachings of the present invention. Accordingly, such modifications are intended to be included within the scope of the present invention as defined in the claims.

The invention claimed is:

1. A probe for selectively capturing substantially separate phases from a multiphase fluid mixture flowing through a flowline, comprising:
  a) a probe body substantially having the shape of an areofoil, including a terminal end, a basal end, a front portion, a back portion, and lateral portions disposed therebetween, the probe body being shaped and oriented to create a plurality of different pressure regions at different portions of the probe body when the multiphase fluid flows through the flowline, the back portion having the lowest pressure region and the front portion having the highest pressure region of the plurality of different pressure regions;
  b) a first port positioned on the probe body facing in a first direction relative to fluid flowing through the flowline, the first port being positioned in the highest pressure region at the front portion; and
  c) a second port positioned on the probe body facing in a second direction, which is different from the first direction, the second port being positioned outside of the highest pressure region.

2. The probe of claim 1, wherein the second port is positioned at the back portion of the probe.

3. The probe of claim 1, wherein the second port is positioned at the lateral portion of the probe.

4. The probe of claim 1, wherein the first port is an open end of a first conduit included in the probe body, and the second port is an open end of a second conduit included in the probe body.

5. The probe of claim 4, wherein the second port comprises a plurality of open ends of the second conduit included in the probe body.

6. The probe of claim 1, further comprising a third port positioned on the probe body facing in the first direction.

7. The probe of claim 5, wherein the third port is an open end of a third conduit included in the probe body.

8. A probe for selectively capturing substantially separate phases from a multiphase fluid mixture flowing through a flowline, comprising:
  a) a probe body substantially having the shape of an areofoil, including a terminal end, a basal end, a front portion, a back portion, and lateral portions disposed therebetween, the probe body being shaped and oriented to create a plurality of different pressure regions at different portions of the probe body when the multiphase fluid flows through the flowline, the back portion having the lowest pressure region and the front portion having the highest pressure region of the plurality of different pressure regions
  b) a first port positioned on the front portion of the probe body adapted to capture a relatively high density fluid phase from the multiphase fluid flowing through the flowline, the first port being positioned in the highest pressure region at the front portion;
  c) a second port positioned on the back portion of the probe body adapted to capture a relatively low density fluid phase from the multiphase fluid flowing through the flowline, the second port being positioned in the lowest pressure region.

9. The probe of claim 8, further comprising a third port positioned on one of the lateral portions of the probe body adapted to discard one of the captured phases back into the flow line.

10. A probe for selectively capturing substantially separate phases from a multiphase fluid mixture flowing through a flowline, comprising:
- a) a probe body substantially having the shape of an areofoil, including a terminal end, a basal end, a front portion, a back portion, and lateral portions disposed therebetween, the probe body being shaped and oriented to create a plurality of different pressure regions at different portions of the probe body when the multiphase fluid flows through the flowline, the back portion having the lowest pressure region and the front portion having the highest pressure region of the plurality of different pressure regions;
- b) a first port positioned on the front portion of the probe body adapted to capture a predominantly oil phase from the multiphase fluid flowing through the flowline, the first port being positioned in the highest pressure region at the front portion;
- c) a second port positioned on the front portion of the probe body adapted to capture a predominantly water phase from the multiphase fluid flowing through the flowline, the second port being positioned in the highest pressure region at the front portion;
- d) a third port positioned on the back portion of the probe body adapted to capture a predominantly gas phase from the multiphase fluid flowing through the flowline, the third port being positioned in the lowest pressure region.

11. The probe of claim 10, wherein the first port is positioned near the terminal end of the probe body, and the second port is positioned near the basal end of the probe body.

12. The probe of claim 10, wherein the third port is further adapted to discard the any phase of the multiphase fluid back into the flowline.

13. The probe of claim 10, further including a port positioned at the terminal end of the probe body adapted to measure the flowline pressure.

14. A method for selectively capturing substantially separate phases from a multiphase fluid mixture flowing through a flowline, comprising:
- a) providing a probe body substantially having the shape of an areofoil, including a terminal end, a basal end, a front portion, a back portion, and lateral portions disposed therebetween, the probe body being shaped and oriented to create a plurality of different pressure regions at different portions of the probe body when the multiphase fluid flows through the flowline, the back portion having the lowest pressure region and the front portion having the highest pressure region of the plurality of different pressure regions;
- b) placing the probe in the flowline, the probe being oriented such that at least one first port faces upstream with respect to the direction of flow of the multiphase fluid mixture and is located in the highest pressure region, the probe further being oriented such that at least one second port faces downstream with respect to the direction of flow of the multiphase fluid mixture;
- c) using the at least one first port to selectively capture a fluid which has a relatively high density from the multiphase fluid mixture flowing through the flowline; and
- d) using the at least one second port to selectively capture a fluid which has a relatively low density from the multiphase fluid mixture flowing through the flowline.

15. The method of claim 14, further comprising using at least one other port not facing upstream for selectively discarding at least one captured fluid into the flowline.

16. The method of claim 14, wherein the multiphase fluid mixture comprises hydrocarbon oil, water and gases.

17. The method of claim 16, wherein the fluid which has a relatively low density includes substantially the gases, and the fluid which has a relatively high density includes substantially the hydrocarbon oil or water.

* * * * *